United States Patent [19]

Vadgama et al.

[11] Patent Number: 5,547,561
[45] Date of Patent: Aug. 20, 1996

[54] SENSOR DEVICES AND METHOD OF USING SAME

[75] Inventors: Pankaj M. Vadgama, Manchester; Ian M. Christie, Stockport; Yazid M. Benmakroha, Manchester, all of United Kingdom

[73] Assignee: The Victoria University Of Manchester, Manchester, England

[21] Appl. No.: 374,739
[22] PCT Filed: Jul. 23, 1993
[86] PCT No.: PCT/GB93/01565
§ 371 Date: Apr. 3, 1995
§ 102(e) Date: Apr. 3, 1995
[87] PCT Pub. No.: WO94/02584
PCT Pub. Date: Feb. 3, 1994

[30] Foreign Application Priority Data

Jul. 28, 1992 [GB] United Kingdom ............... 9215971

[51] Int. Cl.⁶ ..................... G01N 27/40; G01N 27/404
[52] U.S. Cl. .................. 205/793; 204/403; 204/415; 205/778; 205/792
[58] Field of Search ............... 204/153.12, 153.18, 204/403, 415; 205/778, 792, 793

[56] References Cited

U.S. PATENT DOCUMENTS 4,388,166  6/1983  Suzuki et al. ........................ 204/403
4,678,698  7/1987  Mencke ............................... 428/171
4,832,797  5/1989  Vadgama et al. .................... 204/415

FOREIGN PATENT DOCUMENTS 216577  4/1987  European Pat. Off. .
225094  6/1987  European Pat. Off. .
503943  9/1992  European Pat. Off. .

Primary Examiner—T. Tung
Attorney, Agent, or Firm—Cushman Darby & Cushman, L.L.P.

[57] ABSTRACT

Sensor devices for detecting components in fluid samples, especially by electrolytic analytical methods, comprising a detecting means (usually an anode, especially one of platinum) surrounded by a selectively permeable membrane barrier composed of a mixture of polyvinyl chloride and polyaryl sulphone polymers. Preferred proportions of the polymers are 1 to 9 parts of polyaryl sulphone for each part of polyvinyl chloride, and the mixture may be formed into membranes by solution casting. Preferably this barrier is used with an inner membrane, especially of porous polycarbonate. In use, these polymer mixtures are especially useful in their selective permeability to glucose. Also provided are methods for their use in analysis, and the polyvinyl chloride/polyaryl sulphone polymer compositions themselves and membranes made from them.

20 Claims, No Drawings

SENSOR DEVICES AND METHOD OF USING SAME

This invention relates to sensor devices such as are used in the determination of a component or components which may be present in a fluid sample, such as a physiological fluid (e.g. blood) or other fluids of biological origin (e.g. fruit), process fluids or effluents.

BACKGROUND OF THE INVENTION

Many forms of sensor have been proposed, and commonly these rely on some form of membrane to control the extent to which the components present in a sample under examination can gain access to an electrode, at which they can then be detected and determined. Especially, it well known to make sensors using membranes to separate the media being analysed from the active electrode itself. The main function of the membrane is to separate, as far as possible, those components which are desirable (i.e. can take part in the reactions at the electrode on which the desired determination depends) from interferents (i.e. compounds which may be present but are undesirable because they either interfere with the progress of the desired determination reactions or take part in reactions of their own which compete with those of the component sought and distort or overwhelm the signals which are to be measured. The forms of construction have much in common with each other, and mainly differ in the nature of the membrane or media within it or combined with it in some way.

Some forms of sensor rely on the components used to make the membrane, while others rely on the mode of fabrication of the membrane, selecting its physical properties (for example its porosity) or treatments given to it, as these factors can control its effectiveness and selectivity in use, or to the conditions under which the sensor is used.

Other forms of sensors incorporate an enzyme, which converts one substrate compound or analyte into another which may then be more easily measured. Especially, it is known to use oxidase enzymes, which generate hydrogen peroxide—a substance which can be measured very conveniently and very accurately by electrolytic methods, especially amperometrically.

An example is European Patent No. 216577 (of ICI PLC) which specifies an enzyme electrode sensor with membrane barrier of low (>5%) porosity.

Materials which have been proposed for the fabrication of membranes for sensors include polyvinyl chloride (PVC)—but it has been stated to be essential for it to be only in plasticized form, as described in European Patent Application No. 92302131.5.

It has also in proposed in European Patent Application No. 86308918.1 (Publication No. 225094) to use a sulphonated or unsulphonated polyaryl sulphone as membrane for a sensor of the enzyme electrode type.

The known sensors, utilising various membrane materials, are very valuable in analytical techniques and the analysis of biological fluids (e.g. blood) for the presence of substances considered critical for medical reasons—e.g. glucose and other materials which may be oxidisable or reducable, or have toxic properties. However, they are not entirely satisfactory in use, as membranes which are permeable to glucose are usually also permeable to other compounds which interfere with the analytical determination of the glucose. Membrane materials vary in the degree of permeability or selectivity towards various species which may be present in samples to be examined, so no membrane material is universally appropriate and the choice depends partly upon the particular application for which it is to be used.

It is common to require a sensor to be highly selective or, at least, to be very efficient at excluding compounds which can interfere with the accuracy of the detection and determination of a desired chemical species, for example at an electrode surface. It is also desirable to have a form of sensor which can be used with accuracy at higher concentrations of glucose than are practicable with the conventional sensors and study media.

SUMMARY OF THE INVENTION

We have now found that the selectivity of such a membrane-enclosed sensor can be significantly and surprisingly modified and improved by making the membrane of a mixture of polyvinyl chloride and a polyaryl sulphone, and that this mixture of polymers is surprisingly superior to either polymer component used alone, especially in its permeability to glucose.

Thus according to our invention we provide an improved sensor device comprising means for detecting components present in fluid samples and providing an output representative of the content of said component, comprising the said detecting means and a membrane barrier between the detecting means and the sample to be analysed, characterised in that the membrane barrier is composed of a combination comprising at least one polyvinyl chloride and at least one polyaryl sulphone.

According to a further feature of our invention we also provide a method for determining a component (an analyte) in a fluid sample, which comprises contacting the sample with a sensor device as defined above. This is done especially by bringing the sample into contact with the membrane and measuring the response of the measuring means to the desired component (especially glucose) which has diffused through the membrane.

We also provide new polymer compositions, useful for making membranes having selectively permeable properties appropriate for incorporation in sensors for analytical and instrumental purposes, characterised in that they comprise a combination of at least one polyvinyl chloride and at least one polyaryl sulphone, and membranes made therefrom.

DETAILED DESCRIPTION OF THE INVENTION

For convenience of description herein, we use the abbreviation "PVC" for the polyvinyl chloride and "PS" for the polyaryl sulphone.

Especially, in the devices and method of our invention, the sensor device comprises a detecting means in contact with an electrolyte medium and beth are enclosed by a membrane of mixed PVC and PS polymers which provides an interface for contact with a sample to be analysed.

The polyvinyl chloride (PVC) may be any polymer of vinyl chloride, as for example those made and available commercially, The molecular weight of the PVC is relatively non-critical to the present invention; most commercial grades can be used satisfactorily, and the grade most appropriate for any particular use can be determined readily by sample trial. A typical and convenient molecular weight is in the range 10,000 to 200,000 but products outside this range and mixtures of different molecular weight materials may be used if desired.

The polyaryl sulphone (PS) may be a sulphonated or an un-sulphonated material, or a mixture of two or more thereof. It may be used in a variety of forms, for example a product comprising mainly one structure fitting the description "polyaryl sulphone" or it may be a mixture of such components having different structure or molecular configuration characteristics. Conveniently, it may be a commercially available product.

The polyaryl sulphone may be, for example, any of those compounds disclosed and more fully described in European Patent No. 22509, referred to therein as "sulphonated or un-sulphonated polyaryl sulphones" and, in abbreviated form, as "PAS." These are described as polymers containing repeating units of the general formula—(—Ar—Y—)— wherein Ar represents a divalent aromatic radical and optionally, but preferably, at least some of the Ar groups are sulphonated, and Y represents—$SO_2$—. The group Ar is preferably a group containing at least two aromatic rings fused together or linked together by a direct bond or linked together by an aliphatic group, an oxygen atom or sulphur atom or a sulphone group. The details and disclosures of that European Patent concerning the sulphone polymers is incorporated herein by reference, including the statement that some of the said polymers or copolymers are disclosed in and can be made by methods described in European Patent No. 8894.

It is preferred that the two types of polymer component (PVC and PS) should be, as far as is reasonably practicable, miscible with each other. So, it is preferred that the membranes made from them for the purposes of this invention are made by mixing the components thoroughly and intimately.

The membrane material (i.e. the mixture of two polymers PVC and PS) may be made into membranes by any known or conventional method. Most conveniently, this can be done by solution-casting techniques, using solvents to dissolve the polymers and then spreading the solution on a plate or flat surface and allowing the solvent to evaporate, leaving the polymers deposited as a film on the flat surface—from which it can then be removed for use. The solvents which may be used for this vary, and any of those known in the art (individually or as mixtures) may be used. It may not always be practicable to use the same solvent for both the PVC and the PS, so a very convenient procedure is to dissolve the PVC and PS separately in solvents best suited to each of them, and then to mix the resulting solutions in whatever proportions are considered most appropriate to obtain the desired proportion of the two polymers in the final deposited film. Among the various solvents which may be used, a convenient one for dissolving the PVC in particular is tetrahydrofuran (THF). This solvent casting method has the advantage of ensuring that the polymers are mixed as intimately as possible.

It is preferred that the polymer composition of PVC and PS also comprises a plasticizer. This may be any compound which has the property of plasticizing the components polymer or polymers, especially the PVC, and there is a wide variety of commercially available products to choose from. An example of a preferred plasticizer is isopropyl myristate (IPM). The proportion of the plasticizer may vary considerably, and the optimum amount for any particular purpose can be determined by simple trial. In general, the proportion may be calculated as that appropriate for plasticizing the amount of the PVC component used, and the proportion required in relation to the combined PVC and PS diminishes as the proportion of PVC in the mixture decreases. When a plasticizer is used, it may be incorporated in any known manner, but most conveniently by inclusion in the solution used for solution-casting—either by adding it as such to the final solution of the mixed polymers or by adding it in solution in one or other of the solutions of the component polymers or dissolved in a separate solvent.

The detecting means is most conveniently of one of an electrochemical nature, but other types (e.g. spectrophotometric or optical detecting systems) may be used if desired. The detecting means will usually comprise an electrode system and a liquid or gel phase electrolyte-containing medium. In most applications the electrolyte will be aqueous (i.e. aqueous or aqueous-based) but the use of non-aqueous electrolyte media (for example organic-based media) is not excluded.

The active electrode may be any of those known in the art, for example a metal electrode, but especially a platinum anode. This is most conveniently made in combination with a silver/silver chloride counter-electrode, as for example in the so-called Clark electrode, which comprises a platinum electrode surrounded by a silver/silver chloride ring.

The sensor device of our invention can have a single membrane or, if desired, multiple layers of membrane material. When multiple layers of membrane are used, these may be the same or different, but we prefer that the outermost membrane, i.e. the one which furthest from the active electrode and is contacted with the sample under examination, is made of the membrane composition (mixed PVC and PS polymers) defined according to this invention. This arrangement gives the greatest contribution to determining the access of the components present in the sample to the active electrode surface.

When multiple membrane layers are used, the inner membrane layer or layers (i.e. one or more layers which lie within the outermost one, nearer to the active electrode itself and not in direct contact with the sample under examination) may be made of a wide variety of materials, as is known in the art. We prefer, however, that such an inner membrane is made of a porous film of polycarbonate. Alternatives include membranes (e.g. dialysis membranes) made of cellulose or cellulose derivatives. When the PVC/PS membrane is used as the outermost layer, and thereby this excludes substantially all the interferents likely to be of concern, then this allows greater freedom of choice of the material of any inner membrane which m,ay be used—even towards the ideal of an inner membrane being only non-diffusion limiting, as the outermost layer will have provided the necessary screening from interferents.

The proportion of the two polymer components (PVC and PS) used to form the membrane may vary, and the proportion chosen for use in any particular case will depend upon such factors as the degree of selectivity desired and, of course, cost and ease of making it. The most advantageous proportion is when the two components are in approximately 3:1 (PS:PVC) or 75/25, as the permeability to glucose at that ratio can be as much as 10 or even 100 times as great as it is for membranes made of the individual components (PVC or PS alone). The exact degree of enhancement of glucose permeability depends, of course, on the precise details and conditions involved, and this figure of up to 100 times will not necessarily be attained in every possible circumstance. As it will be appreciated, such a great increase, though welcome, is not essential for practical utility, so useful results can still be obtained when the proportions are more or less than this particular proportion—and particularly in the range 1 to 9 parts of PS for each part of PVC, though proportions outside these ranges may be used if desired. The proportions are expressed here as ratios by weight.

The thickness of the membranes can be of the order abready used conventionally in the art, but may be varied as found most appropriate having regard for the particular mixed polymer composition being used and the conditions under which it is to be used. Thus a convenient thickness is in the range 10 to 40 μm, though larger or smaller thicknesses can be used if desired.

Use of the sensor is in the conventional electrode cells. These can be polarized at the conventional potentials appropriate for the determination procedure, and using conventional media. Thus, a polarization at +650 mv in the usual phosphate/chloride buffer is usually most convenient except when the pH is raised from 7.4 to 13 (as discussed below) and the buffer and the polarization may be altered to suit the high pH used.

An advantage of the sensors and the membrane materials now specified in the selective diffusion of a sugar, especially glucose, through the membrane. Work with the improved sensors of the present invention shows a vast greater diffusion of glucose through the mixture of polymers than through either polymer alone. This is both highly surprising and very useful. This permeability to the glucose is especially noteworthy as it is associated with the ability to hold back (i.e. remain impermeable to) other components commonly present in media (especially biological fluids and media, for example blood) which interfere greatly with the detection of the glucose for clinical, monitoring or diagnostic purposes. Such interferents include ethanol, paracetamol, uric acid, phenolics, and the like.

Glucose sensors can be made which directly oxidise glucose at the electrode (anode) without any enzymatic action or the step of generation of hydrogen peroxide. This is very similar to other electro-analytical procedures, in which a component (e.g. paracetamol) is oxidised.

Up till now we have not been aware of any method by which the screening out of interferents (i.e. components which are electro-active but interfere with the determination of the selected component which it is desired to measure—particularly glucose) has been achieved by the use of a selective membrane. Surprisingly, the mixed membrane composition PS/PVC has this property, and screens out such compounds as paracetamol, ascorbate and urate while being permeable to glucose.

There are two principal forms of construction which may be used to secure the advantages of the new membrane material we now propose. In one, an enzyme is present and in the other it is not present.

Using an enzyme, the basic construction sequence is:

SAMPLE
MEMBRANE (PVC/PS MIXTURE)
ENZYME
INNER MEMBRANE (E.G. POLYCARBONATE)
ELECTRODE.

The alternative form, without an enzyme, preferably has the construction sequence:

SAMPLE
MEMBRANE (PVC/PS MIXTURE)
SOLUTION AT HIGH pH
ELECTRODE.

In this second form, a high pH is necessary to render electroactive the glucose diffusing through the membrane. By "high pH" we mean a pH of at least 10, and preferably in the range 12 to 14. A good and convenient pH is approximately 13.

For these, the components (apart from the PVC/PS membrane) are mainly the conventional ones, and the many variants known in the art may be used.

The permeability of the PVC/PS membrane is most marked with glucose, and this is seen as the basis for the most important and surprising effect and its most important utility. The effect is not limited solely and absolutely to glucose, and other sugars can diffuse through it and be detected at high pH, like glucose, at an electrode, and so be detected and determined by means of the sensors and methods of the present invention. PVC and PS (and mixtures of PVC and PS) all have the ability to retain a stable high pH environment below the membrane, and so are very suitable for this form.

Although the current values are low, the extreme selectivity renders such signals adequate for meaningful measurement. Thus, direct glucose oxidation at a Clark electrode using a 20 mM solution of glucose shows a virtually zero response when the membrane is PVC or PS alone, but a response of over 100 nA for a 3:1 mixture of PS and PVC (PS:PVC). Using hydrogen Peroxide at 1 mM contentraton, an increase in response occurs as the proportion of PS added to PVC increases, but without any dramatic signs of selectivity at intermediate proportions. Using paracetamol at 1 mM concentration, a substantial response occurs for pure PVC but this falls off rapidly towards zero as PS is added to the PVC and reaches almost zero at the 3:1 PS:PVC.

Extremely high concentrations of glucose can be measured with this technique, with remarkable selectivity against common interferents and no loss of linearity. For example, at pH 13 linear response (signal/concentration) has been demonstrated for glucose concentrations up to 600 mM (108 grams per litre) and beyond—with direct response of about 95 nA at the 600 mM level for the high pH sensor without enzyme but with a mixed PVC/PS membrane and only the sensor structure sequence:

Sample/mixed PVC.PS membrane/solution pH 13/electrode.

(preferably with a thin underlying dialysis membrane to act as a thin layer of electrolyte to stop the anode and cathode being insulated from each other by the plastic membrane).

Such glucose concentrations are far beyond clinical glucose levels, but indicates the range of applicability and other uses, for example in the food and brewing industries. The usefulness can be seen when one realises that the glucose concentrations to which the invention is applicable are of the order of up to 10% weight/volume, or even higher.

The advantage of the use of a high pH is that it enables glucose to be measured without oxygen dependence—i.e. there is no need to generate hydrogen peroxide in order to get a signal, and as there is no need to produce hydrogen peroxide there is then no need for either an enzyme or oxygen. This simplifies the task of sensor construction and avoids dependence on the presence of oxygen or enzyme—both of which are factors which can limit the system and the components which it can be used to determine. This gives the sensor of the present invention a much wider scope of applicability than the glucose oxidase sensors to date.

Thus, as examples of uses which present difficulties for use of the conventional enzyme electrodes, but which can be dealt with much more easily by the sensors of the present invention, there may be mentioned measurements in oxygen-deprived tissues (e.g. in tumours), in fruit and fruit products, in sugar manufacture, and in industrial fields for study or monitoring of process solutions or other media, or of industrial effluents. For example, our sensors can be applied to the study of fruit juices or to fruit as such, for it is not necessary to isolate the fruit juice stud contact with a cut surface or by insertion into fruit, to secure a simple juice/sensor contact, can be quite sufficient for use in study and evaluation.

The invention is illustrated but not limited by the following Example, in which the parts and percentages are by weight unless otherwise stated.

EXAMPLE

Using a grade of polyaryl sulphone (PS) supplied by a commercial company (ICI PLC), the following solutions were prepared:

Solution 1:
  0.4g of the PS in
  7.5 mls of dimethylformamide +2.5 mls of 2-methoxyethanol.

Solution 2:
  0.06 g of polyvinyl chloride (PVC) and 150 µl of isopropyl myristate (IPM) in 5 mls of tetrahydrofuran.

The two solutions were then mixed in ratios 3:1, 1:1 and 1:3 by volume, thus totalling 6 mls each (solutions 1 and 2 in amounts of 4.5 ml:1.5 ml, 3 ml:3 ml and 1.5 ml:4.5 ml) and the 6 ml solutions were poured out into petri dishes and left open to the atmosphere for the solvent to evaporate and the residue to dry.

The resulting plastic films or membranes were formed:

| Ratio of Solution 1 to Solution 2 | Ratio of polymers in membrane | | IPM content in the whole membrane |
| --- | --- | --- | --- |
| | PS | PVC | |
| 1:3 | 52.4% | 47.6% | 135 µl |
| 1:1 | 76.6% | 23.4% | 90 µl |
| 3:1 | 90.9% | 9.1% | 45 µl |

Using a grade of polyaryl sulphone (PS) supplied by another commercial company (Aldrich Chemical Company), solutions were prepared as above except that Solution 1 was made by dissolving 0.4 g of the PS in 10 ml of tetrahydrofuran. Solution 2 was made as described above. Mixing and casting 6 ml portions in petri dishes to dry and form films was repeated, as described above.

The films or membranes made as described above were used as the membrane component of a sensor sell comprising a platinum anode and a surrounding silver/silver chloride ring in a Clark electrode assembly, and were found to show high permeability in favour of glucose when contacted with aqueous solutions containing glucose and various contaminants, e.g. paracetamol.

We claim:

1. A sensor device for detecting components present in fluid samples and providing an output representative of the content of said component, comprising a detecting means and a membrane barrier between the detecting means and a sample to be analyzed, wherein the membrane barrier is composed of a combination of polymer components comprising a mixture of polyvinyl chloride and a polyaryl sulphone.

2. A sensor device as claimed in claim 1 wherein the detecting means is in contact with an electrolyte medium and both are enclosed by a membrane of a mixture of polyvinyl chloride and polyaryl sulphone polymers which provides an interface for contact with a sample to be analyzed, the said membrane having a thickness in the range of 10 to 40 µm.

3. A sensor device as claimed in claim 1 or claim 2 wherein the polymer components used in the mixture are miscible with each other.

4. A sensor device as claimed in claim 1 or claim 2 wherein the polymer components for the membrane comprising the polyvinyl chloride and the polyaryl sulphone are mixed and formed by solution casting.

5. A sensor device as claimed in claim 1 or claim 2 wherein the proportions of the polymer components comprising the polyvinyl chloride and the polyaryl sulphone used to form the membrane are in the range 1 to 9 parts of the polyaryl sulphone for each part of the polyvinyl chloride, by weight.

6. A sensor device as claimed in claim 1 or claim 2 wherein the polyvinyl chloride used has a molecular weight in the range 10,000 to 200,000.

7. A sensor device as claimed in claim 1 or claim 2 wherein the polyaryl sulphone is sulphonated or un-sulphonated, or a mixture thereof.

8. A sensor device as claimed in claim 1 or claim 2 wherein the mixture of the polymer components comprising the polyvinyl chloride and the polyaryl sulphone contains one or more plasticizers.

9. A sensor according to claim 8 for determining a component in a fluid sample wherein the plasticizer is isopropyl myristate.

10. A sensor device as claimed in claim 1 or claim 2 wherein the detecting means comprises a platinum electrode.

11. A sensor device as claimed in claim 10 wherein the electrode is used as an anode in conjunction with a silver/silver chloride cathode.

12. A sensor device as claimed in claim 1 or claim 2 wherein the polyvinyl chloride/polyaryl sulphone membrane barrier constitutes an outer membrane layer in conjunction with an inner membrane which is made of a porous film of polycarbonate.

13. A sensor device as claimed in claim 1 or 2 wherein an enzyme is present.

14. A method for determining a component in a fluid sample, using a sensor device as claimed in claim 1 or claim 2, which comprises bringing the sample into contact with the membrane barrier and measuring a response of the detecting means to the component which has diffused through the membrane barrier.

15. A method as claimed in claim 14 wherein the component in the fluid sample being determined is glucose.

16. A sensor device comprising a membrane selectively permeable to a sugar by diffusion while excluding interferants present in a sample to be analyzed comprising a mixture of polyvinyl chloride and a polyaryl sulphone.

17. A sensor comprising a membrane selectively permeable to a sugar while excluding interferants appropriate for incorporation in sensors for analytical and instrumental purposes comprising a polymer composition which is a mixture of polyvinyl chloride and a polyaryl sulphone.

18. A sensor according to claim 17, wherein said membrane further comprising a plasticizer.

19. In a method of detecting and measuring the presence of an analyte in a fluid sample by a membrane enclosed sensor system, the improvement which comprises a permeable membrane comprising a polymer matrix of a mixture of polyvinyl chloride and a polyaryl sulphone wherein the membrane is selectively permeable to the analyte which diffuses through the polymer matrix while excluding interferants present in the fluid sample.

20. A method according to claim 19, wherein the amount of polyaryl sulfone in the membrane ranges from 1 to 9 parts for each part of polyvinyl chloride and the polymer matrix further comprises a plasticizer.

* * * * *